United States Patent
Perkins et al.

(12) 
(10) Patent No.: US 6,193,949 B1
(45) Date of Patent: Feb. 27, 2001

(54) METHOD OF SIRE SELECTION USING NALOXONE CHALLENGE TESTS AND KITS THEREOF

(75) Inventors: Anne Perkins, East Helena, MT (US); James A. Fitzgerald, Columbus, MS (US); Verne A. Lavoie, Dubois; John N. Stellflug, Idaho Falls, both of ID (US)

(73) Assignees: The United States of America as represented by the Secretary of Agriculture, Washington, DC (US); Carroll College, Helena, MT (US)

(*) Notice: Subject to any disclaimer, the term of this patent is extended or adjusted under 35 U.S.C. 154(b) by 0 days.

(21) Appl. No.: 09/320,653

(22) Filed: May 27, 1999

(51) Int. Cl.$^7$ .......................... A61K 49/00; A61K 31/44
(52) U.S. Cl. .......................... 424/9.1; 424/9.1; 514/282
(58) Field of Search .................. 514/282; 424/9, 424/9.1

(56) References Cited

PUBLICATIONS

A. Perkins, J.A. Fitzgerald, and E.O. Price, "Luteinizing Hormone and Testosterone Response of Sexually Active and Inactive Rams," J. Anim. Sci. 70:2086–2093 (1992).

J.A. Fitzgerald and A. Perkins, "Effect of Morphine and Naloxone on LH Response and Sexual Behavior of Rams (Ovis Aries)," Domestic Animal Endocrinology 11(3):271–279 (1994).

A. Perkins, J.A. Fitzgerald, and E.O. Price, "Sexual Performance of Rams in Serving Capacity Tests Predicts Success in Pen Breeding, " J. Anim. Sci. 70:2722–2725, (1992).

J.A. Fitzgerald and A. Perkins, "Sexual Behavior of Rams: Biological Perspective to Flock Management," Sheep Research Journal 9(2):51–58 (1993).

*Primary Examiner*—Richard L. Raymond
*Assistant Examiner*—Ben Schroeder
(74) *Attorney, Agent, or Firm*—Thanda Wai; M. Howard Silverstein; John D. Fado

(57) ABSTRACT

There is variation in the sexual performance of male mammals. The purpose of this invention is to help identify high sexual performing males, particularly for livestock such as sheep. Testosterone is necessary for the normal execution of male behavior, but baseline levels are not predictive of libido. When a male mammal is given an injection of naloxone (an endorphin antagonist), his testosterone or LH response to the injection predicts whether he is a sexually active or inactive individual. This test is based on the premise that libido is more closely linked to the ability to secrete testosterone rather than baseline concentrations. Naloxone challenge may be used as a general method to predict libido in male mammals.

15 Claims, 3 Drawing Sheets

METHOD OF SIRE SELECTION USING NALOXONE CHALLENGE TESTS AND KITS THEREOF

FIELD OF THE INVENTION

This application addresses the phenomenon of variation in sexual performance of male mammals. The purpose of this invention is to identify sexually active and non-working male mammals.

BACKGROUND OF THE INVENTION

Multiple physiological mechanisms are involved in mediating libido in male mammals. The most well understood process is the hypothalamic-pituitary-gonadal (HPG) axis. The hypothalamus secretes gonadotropic-releasing hormone (GnRH) that causes the pituitary to release luteinizing hormone (LH), which in turn causes the testis to secrete testosterone (T) (see FIG. 1). The HPG axis responds to sexual stimuli in adult males (visual and olfactory) and is dependent on a minimum concentration of plasma testosterone. Yet, individual variation of testosterone concentrations is not predictive of libido or sexual performance once minimum levels are present. It appears that the ability to increase plasma testosterone concentrations in response to sexual opportunities, rather than base line concentrations of testosterone is more important for predicting libido. The ability to change levels of hormones is under the influence of endogenous opiates. Based on data collected mostly in rodents, we know that the HPG axis is influenced by a complex interaction of endogenous opiates and neurotransmitters in the brain. It is well established that endorphins have an inhibitory influence on the release of hypothalamic gonadotropic hormone-releasing hormone (GnRH). Naloxone (an opiate antagonist) can reverse the inhibitory effects of naturally-occurring endorphins on luteinizing hormone. Hence, treatment with naloxone causes significant elevations in serum LH concentrations in rats (Meites et al., 1979) and rams (Ebling et al. 1987). A scheme for this is represented in FIG. 1.

In 1979, Gessa et al. gave injections of naloxone to sexually inactive male rats. The injections induced copulatory behavior. The authors suggested that endogenous opiates were the cause of the sexual inhibition and that the drug naloxone removed the opiate driven sexual inhibition. We gave naloxone to sexually inactive rams, but were unable to induce sexual behavior (Fitzgerald and Perkins, 1994). Unexpectedly, we noticed that the LH response to the naloxone treatment was greater in the sexually active rams versus the sexually inactive rams. So, although naloxone treatments did not alter libido or sexual performance, it did predict which rams would be most likely to demonstrate sexual activity based on their LH concentrations.

There is a great deal of variation in the sexual performance of male sheep. In 1964, Hulet et al. described rams that failed to mate with estrus females during behavioral testing. Since then, several scientists, as well as producers, have observed poor sexual performing rams. Standardized sexual behavior tests have been developed that can evaluate sexual performance in rams (Kilgour and Whale, 1980). These behavioral tests involve observations of sexual activity. The average number of ejaculations that a ram achieves over several sexual performance tests correlates to pasture breeding efficiency (Perkins et al., 1992). These tests, however, are labor intense, costly and impractical for the producer to conduct. The purpose of this project was to develop a more practical tool (a drug test) that could be used by veterinarians or producers to predict sexual performance in rams or other species for which maximizing reproductive success is a concern.

The first and most obvious place to look for a predictor of sexual performance is basal concentrations of testosterone. Testosterone is critical to both the development and execution of sexual behavior in all male mammals. Yet once minimal concentrations of testosterone are present, increasing testosterone concentration will not increase sexual performance (D'Occhio and Brooks, 1976). Most rams, including sexually inactive rams, have the minimal amounts of testosterone needed to execute sexual behavior (Perkins et al., 1992). In addition, variations in testosterone concentrations beyond minimal values are not correlated to sexual performance (Knight, 1973). Therefore, physiological mechanisms located elsewhere (perhaps in the brain and not the gonads) are more likely to be responsible for variations in libido and sexual performance.

We have observed reduced LH responses by poor sexual performing rams to estrus ewes (Perkins et al., 1992). Therefore, we chose to investigate the effect of naloxone, on both sexual behavior and the pituitary-gonadal response among rams that vary in sexual performance. Our original goal was to increase the libido and the sexual performance of low performing rams by increasing LH responses with Naloxone. Although we were unsuccessful in improving the sexual behavior of sexually inactive rams (Fitzgerald and Perkins, 1994), we have now established a predictor (77% accuracy) of sexual performance by measuring the luteinizing hormone and testosterone response to an IV injection of naloxone. We recommend that veterinarians or producers as a tool for screening out low libido or poor sexual performing rams use this protocol. This naloxone test will also help in the identification of high sexual performing rams, but it will not screen for sexual orientation. This same prediction might be true for any male mammal that expresses individual variations in both libido and endogenous opiate levels in mammals such as: humans, primates (such as monkeys), felines, canids, rodents, marine mammals, ungulates (such as elk, deer, antelope, caribou, among others), and livestock such as rams, bulls, stallions, boars, among others. The ram has been an excellent model for examining this system.

SUMMARY OF THE INVENTION

The present invention relates to a method of identifying sexually performing male mammals. Testosterone is necessary for the normal execution of male behavior, but baseline levels are not predictive of libido. When a male mammal is treated with naloxone, an endorphin antagonist, his LH and testosterone response to the treatment predicts whether he is a high or low sexual performing ram. A positive response of testosterone to naloxone challenge in the male mammal is predictive of a sexually active male mammal, whereas a lack of response is predictive of a non-working male mammal. This test is based on the premise that libido is more closely linked to the ability to secrete testosterone rather than to the baseline concentrations.

The invention provides for a correlation between sexual activity and a LH or testosterone response of male mammals upon treatment with naloxone.

An object of the invention is to discriminate high sexual performing male mammals from low and non-sexual performers by determining the levels of LH or testosterone made in response to challenge by naloxone.

Another object of the invention is a method of identifying sexually active male mammals by treating the individual with naloxone and determining the individuals that exhibit an increase in the levels of LH or testosterone.

A further object of the invention is a method of identifying sexually inactive or non-working male mammals by treating the individual with naloxone and determining the individuals that do not exhibit a large enough increase in the levels of LH or testosterone upon challenge with naloxone.

An additional object of the invention is a method of selecting for sexually active male mammals to be used for breeding Purposes by selecting individuals that exhibit an increase in testosterone made in response to naloxone challenge.

An advantage of the invention is to use sexually active male mammals selected by the methods of this invention to increase the population of endangered species.

Another advantage of the invention is to use individual male mammals selected by the methods of this invention either to increase or to control a specific population of animals kept in captivity.

A further advantage of the invention is to shorten the breeding period and decrease stocking ratios.

Uses and applications of this invention encompass but are not limited to the uses described above.

DETAILED DESCRIPTION OF THE INVENTION

Figure 1:
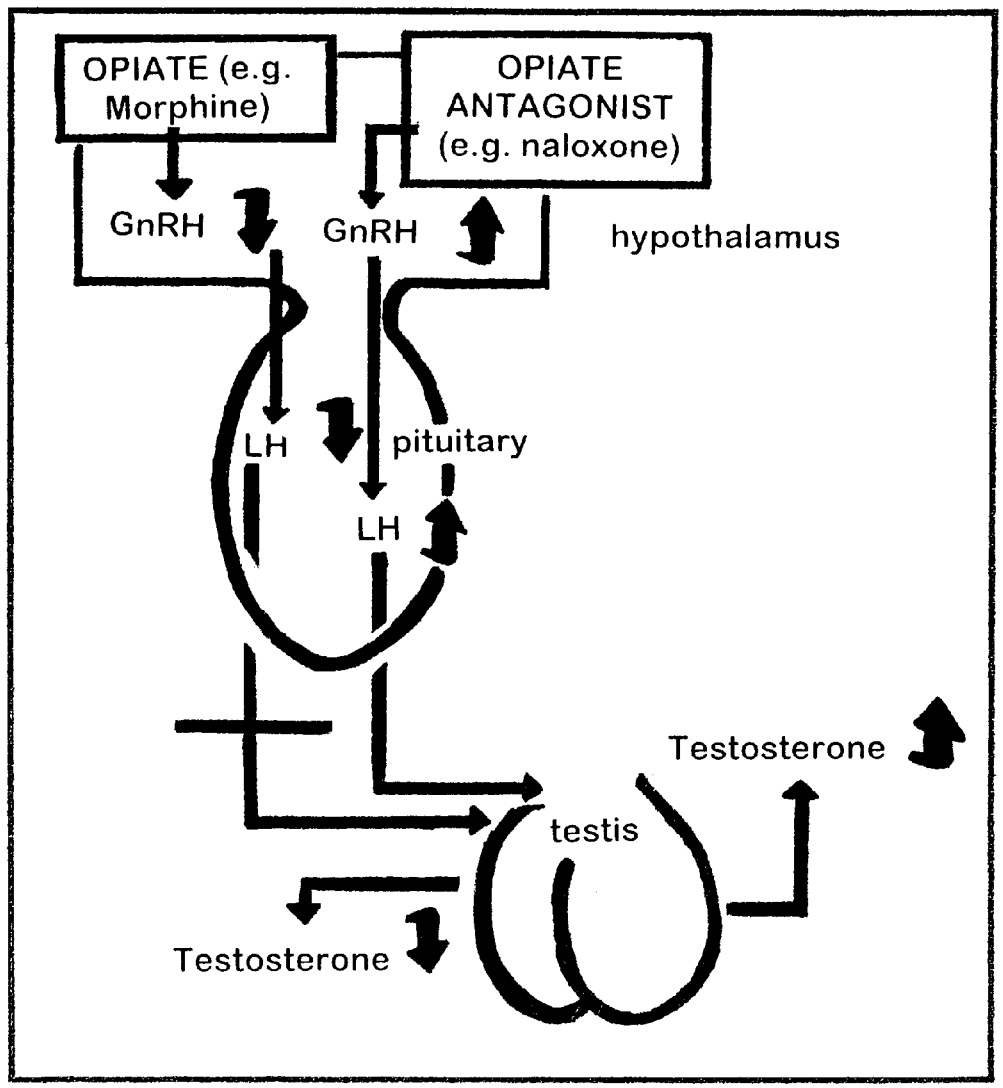
FIG. 1 depicts the pathway by which naloxone challenges the release of both LH and testosterone. Opiates inhibit the release of LH and testosterone, while naloxone removes that inhibition.

The present invention relates to a method of identifying sexually active and inactive male mammals.

The invention is drawn to a method of discriminating sexually active from non-working male mammals (which have endogenous opiates), the method comprising:

(a) administering naloxone to individual male mammals in an amount sufficient to elicit a measurable increase in levels of luteinizing hormone (LH) or testosterone, (b) waiting for a period of time sufficient to elicit a measurable increase in levels of LH or testosterone, (c) taking an aliquot of blood to test levels of LH or testosterone, (d) measuring the levels of LH or testosterone, and (e) classifying individual male mammals as sexually active or inactive based on the levels of LH or testosterone.

The invention is directed further to a method of selecting sexually active male mammals (which have endogenous opiates) according to the method of the instant invention, the method comprising:

(a) administering naloxone to individual male mammals in an amount sufficient to elicit a measurable increase in levels of LH or testosterone, (b) waiting for a period of time sufficient to elicit a measurable increase in levels of LH or testosterone, (c) taking an aliquot of blood to test levels of LH or testosterone, (d) measuring the levels of LH or testosterone, (e) designating individual male mammals as high or low performers based on the levels of LH or testosterone, and (f) selecting sexually active individual male mammals based on the levels of LH or testosterone measured in response to naloxone administration.

The method of administration of naloxone may be oral, aerosol, by catheter; or by intramuscular, intraperitoneal, or intravenous injection; more preferably by catheter or injection; and most preferably by intravenous injection.

The amount of naloxone administered to test individuals may range from 0.10–2.5 mg/kg body weight; more preferably in the range of 0.25 to 1.5 mg/kg body weight; and most preferably at 0.5, 0.75, and 1.5 mg/kg body weight.

The period of time sufficient to elicit a measurable increase in levels of LH is at least 15 minutes and may be taken up to a period of 4 hours after administration of naloxone.

The period of time sufficient to elicit a measurable increase in levels of testosterone is at least 30 minutes; more preferably, at least 45 minutes; and, most preferably, 60 minutes. Samples may be taken up to 4 hours after administration of naloxone.

Aliquots of blood sufficient to give a reproducibly accurate measure of the levels of LH or testosterone are at least 1 ml taken in replicates of at least two for each time point.

The levels of LH or testosterone may be assayed by radioimmunoassay (RIA), enzyme-linked immunosorbent assay (ELISA), or other calorimetric or chemical assay. The most preferred assay is radioimmunoassay (RIA). The best predictor of sexual performance is using both LH and testosterone concentrations. Using LH concentration values at 15 minutes post naloxone treatment times the concentration of testosterone at 60 minutes provides the best predictor of both sexually active and non-working rams.

An individual male mammal is classified as sexually active or non-working based on whether the individual's index score falls within a higher or lower group or category of a bimodal distribution for a group of naloxone-challenged individuals whose LH or testosterone response is described by the formula:

$$\text{Index} = [LH_{time \geq 15\ minutes}] \times [T_{time \geq 45\ minutes}].$$

A sexually active male mammal is an individual whose index score falls within the higher range or subset of a bimodal distribution of a group of naloxone-challenged individuals whose LH or testosterone response is described by the formula:

$$\text{Index} = [LH_{time \geq 15\ minutes}] \times [T_{time \geq 45\ minutes}].$$

A sexual or non-working male mammal is an individual whose index score falls within the lower class or division of a bimodal distribution of a group of naloxone-challenged individuals whose LH or testosterone response is described by the formula:

$$\text{Index} = [LH_{time \geq 15\ minutes}] \times [T_{time \geq 45\ minutes}].$$

Test kits for determining the levels of LH or testosterone in individual male mammals following administration of naloxone according to the method of the present invention may comprise:

(a) naloxone in a composition prepared for delivery to test the individual; and (b) directions instructing the administration of naloxone according to the method described herein and interpretation of the results to classify the test individual as sexually active or inactive.

Test kits for determining the levels of LH or testosterone in individuals following administration of naloxone according to the methods described herein may comprise (a) naloxone in a composition prepared for delivery to test the individual;

(b) reagents used to measure levels of LH or testosterone; and (c) directions instructing the administration of naloxone and method of assaying the levels of LH or testosterone according to the methods described in the instant invention, and interpretation of the results to classify the test individual as sexually active or inactive.

Formula to predict sexual performance. The greatest accuracy for predicting sexual performance is through the use of the following formula.

The LH concentration of the subject at or near 15 minutes following naloxone treatment × (times) the testosterone concentration at or near 60 minutes post naloxone administration. A bimodal distribution of scores will reveal the breaking point for the classification of rams within each population tested. Variations of this formula can be used in the development of a kit that might provide less accuracy but at a reduced cost for example, using only testosterone concentrations or only LH concentrations.

Individual non-working or high sexual performing male mammals are chosen from one of the two bimodal classes derived from the formula given above. Individuals that fall within the lower class of the bimodal distribution may be classified as non-working male mammals. Individuals that fall within the higher class of the bimodal distribution may be classified as high sexual performing male mammals.

A non-working male mammal is defined as an individual male that never ejaculates with females during tests and also does not exhibit sexual behavior toward other males.

High sexual performing male mammals are those that maximize their reproductive efficiency by achieving the most number of ejaculations with different females within a given time period. This varies among species.

The invention will be better understood with the aid of the remainder of the description, which follows and in which reference is made to exemplary embodiments of naloxone challenge of rams according to the invention and to exemplary implementations of the test according to the invention.

It should be clearly understood, however, that these examples and drawings are given solely by way of illustration of the objects of the invention, and that they do not in any way constitute a limitation thereof.

EXAMPLE

Experimental Design. Three experiments were conducted in order to determine if hormone responses to a naloxone injection could be used as a predictor of sexual performance in rams. Variables that were evaluated include: dosage of naloxone, season of the year (breeding and non-breeding season), and repeatability within individual rams over two consecutive years. Rams of known sexual performance (high sexual and non-working rams) were given an intravenous injection of naloxone (one of three different doses) in November, June and December. Luteinizing hormone and testosterone responses to the injections were analyzed by radioimmunoassay. All experimental procedures were performed in accordance with the Institutional Animal Care and Use Committee.

Animals. Rams: Initially over 1000 rams at the U.S. Sheep Experiment Station were tested for sexual performance. Rams were exposed individually to three estrus-induced ewes in a small observation pen for 30 minutes. The total number of ejaculations that each ram achieved during each 30-minute test was recorded. The average number of ejaculations that a ram achieved over several tests is called his serving capacity score. For this project, rams were tested with females eighteen times to determine serving capacity scores on individuals. From the original population, 34 non-working rams were first identified. These non-working rams were then evaluated for sexual orientation. Nine rams were identified as male-oriented and 26 remained as non-working rams. A non-working ram is defined as a ram that never ejaculated with females during eighteen separate tests with estrus ewes and did not exhibit sexual behavior toward other males. Twenty-six high sexual performing rams were also selected for this experiment. High sexual performing rams are defined as rams that achieved serving capacity scores ranging from a low of 0.55 ejaculations/test to a high of 5.4 ejaculations/test over the 18 tests. Rams were between 1 and 2 years of age and were tested between September through December. Breeds of rams included Columbia, Targhee, Polypay and Rambouillet and Finn Crosses.

Ewes: The ewes were ovariectimized and estrus-induced using progesterone pessaries (60 mg of medroxyprogesterone acetate, (Tuco Products, Ontario, Canada). Twenty-four hours before testing with rams, when the pessaries were removed, ewes were injected (intramuscularly) with 50 $\mu$g of estradiol in corn oil. Ewes were considered to be in estrus when they would stand to be mounted by the rams.

Rams were between 18 months and 2 years of age during these experiments. They were managed as a group with routine care and maintenance. They were not exposed to ewes except during testing. Rams were maintained on 3.5 lb. of long stemmed alfalfa and access to water.

Naloxone administration and blood collection. Rams were fitted with an indwelling jugular catheter the day prior to the experiment. On the day of the experiment each ram is placed in a separate pen. Four blood samples are taken once every 15 minutes. Immediately after the fourth sample is taken, a predetermined dosage (1.5 or 0.75 mg/Kg body weight) of naloxone is administered through the catheter. Sampling continues once every 15 minutes for an additional hour. Thus, a total of eight blood samples were collected on each ram. The blood plasma was harvested and assayed for testosterone and luteinizing hormone (LH) concentration.

Statistical analysis. Changes in testosterone and LH concentration are calculated by subtracting the pre-naloxone average concentration of the hormone from each of the post-naloxone values for each ram. The largest difference was considered the individual's "response to treatment". These responses to naloxone were compared between ram groups (non-working rams and high sexual performing rams), over seasons, years, and dosages using statistical tests such as PROC GLM and PROC MIX for repeated measure (SAS). In addition, the correlation coefficient for serving capacity scores and testosterone response was calculated. All dosages of naloxone (0.5, 0.75 and 1.5 mg/kg body weight) were equally effective during the breeding season (November and December the following year), but less effective during the non-breeding season (June). Data from all doses during the breeding season are combined for analysis.

RESULTS

Figure 2:
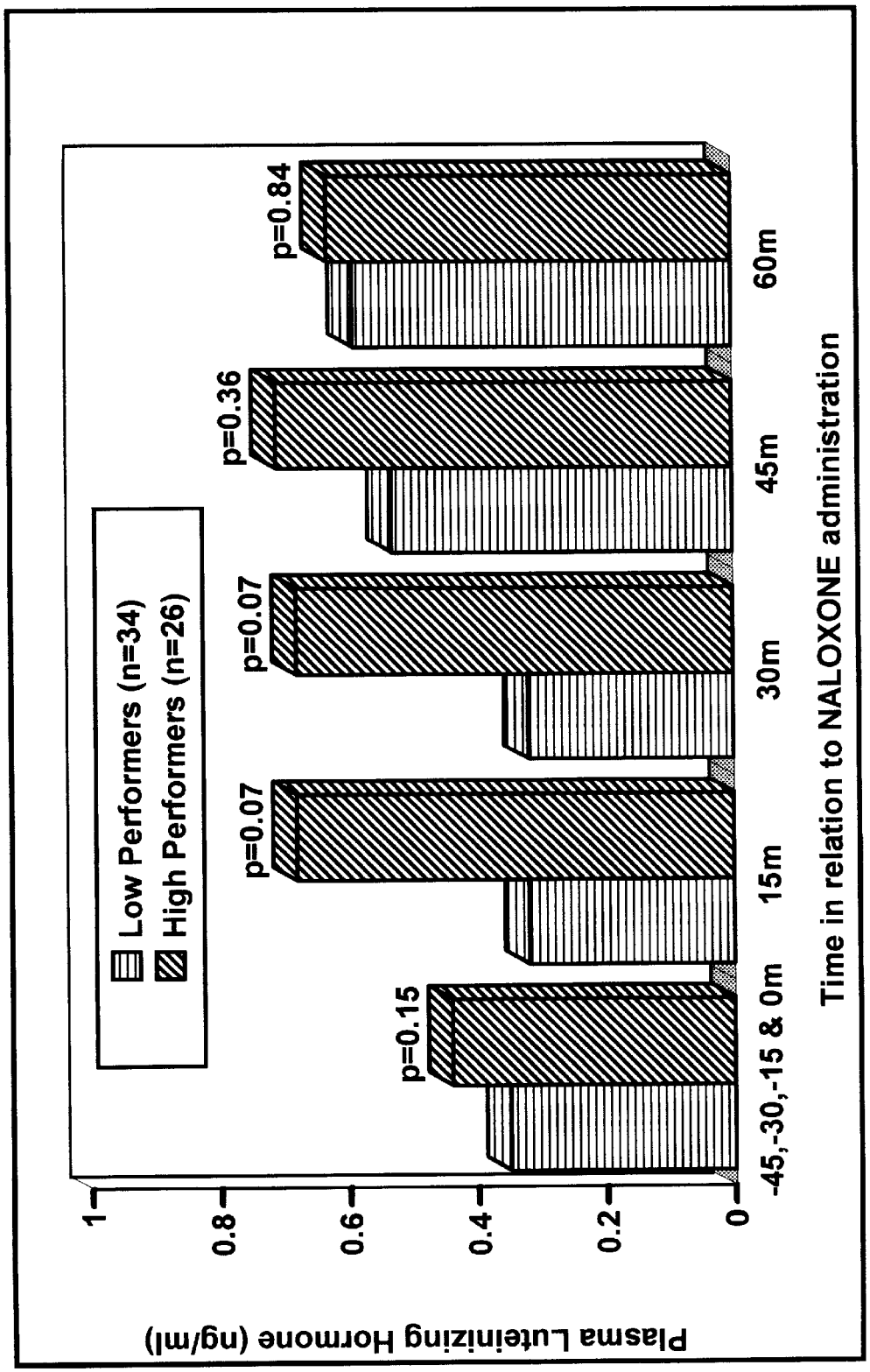
FIG. 2 shows the testosterone concentrations of high sexual performing rams versus the non-working rams. There were no differences prior to the naloxone injection; but 60 minutes following the treatment, there were significant differences between the ram groups.

Testosterone. The testosterone response to naloxone treatment was greater (P<0.05) in the high sexual performing versus the non-working rams. In the high sexual performers testosterone concentrations were higher (P<0.01) 45-min and 60 minutes following the naloxone treatment (6.1±0.9 and 7.7±1.0 ng/ml respectively). In general, the highest value for testosterone concentration was in the last sample taken at 60 minutes post-naloxone treatment. In contrast, the response to naloxone in the non-working rams was only 1.0±1.1 at 45 minutes and 2.3±1.1 at 60 minutes (see FIG. 2). There is not a correlation between serving capacity score and testosterone response to naloxone in sexually active rams during the breeding (r=0.07) or non-breeding (r=0.02) season. This test was not conducted with sexually inactive rams because they all have serving capacity scores of zero (FIG. 2).

Figure 3:
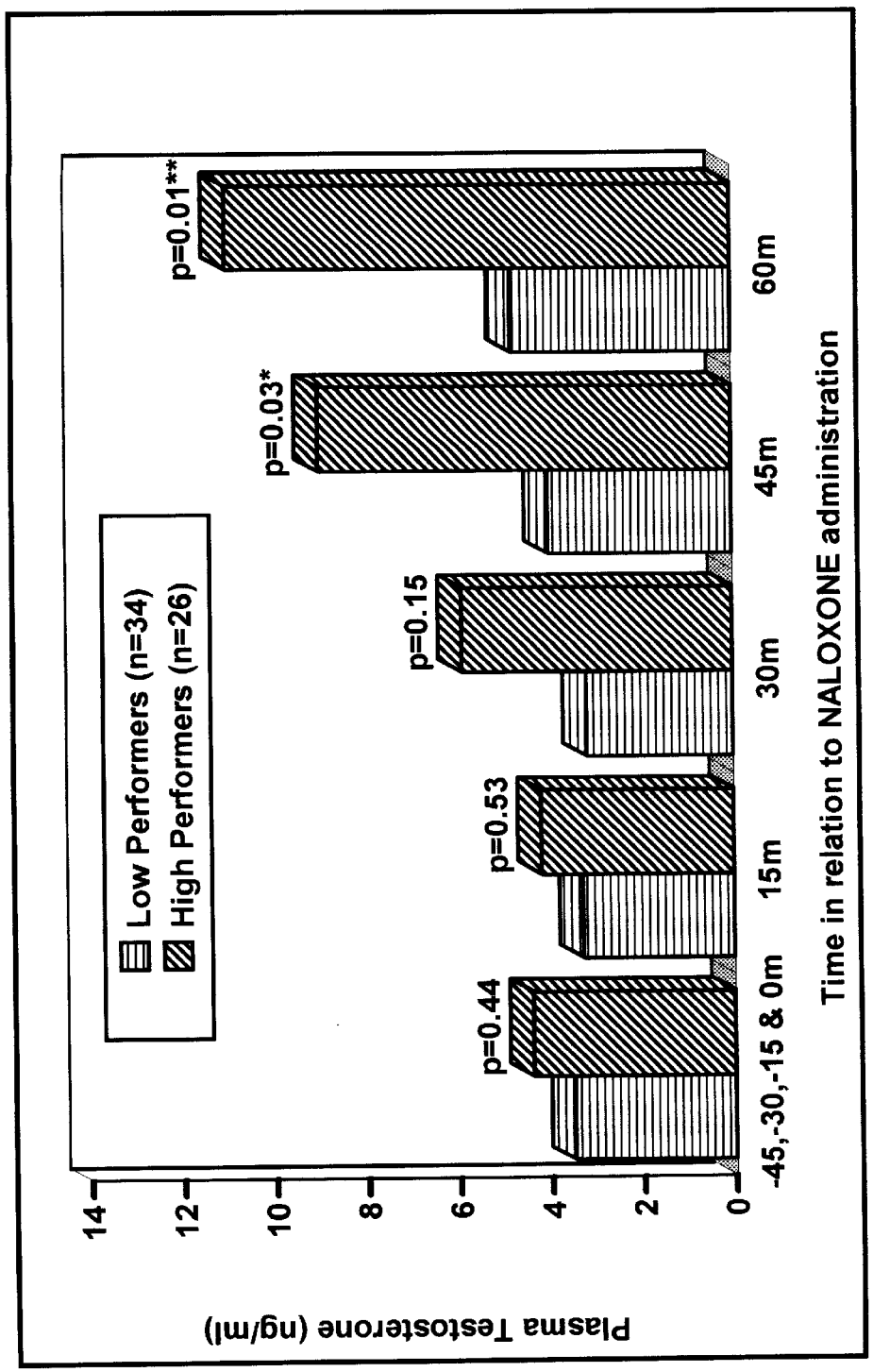
FIG. 3 shows the average values of luteinizing hormone of the high sexual performing rams versus the non-working rams. Prior to the injection of naloxone, there were no differences in the concentrations of LH. At 15 and 30 minutes following treatment with naloxone, LH concentrations between ram groups approached significance differences ($p=0.07$).

Luteinizing Hormone. LH concentrations in response to naloxone tend to differ between sexually active and inactive rams (P<0.07). The LH response to naloxone approaches a significant difference (P<0.07) between non-working and high sexual performing rams at both the 15-minute sample and the 30-minute sample after treatment with naloxone. The three highest LH concentrations were higher (P<0.03) in high performing rams (1.1±0.1) when compared to the non-workers (0.63+0.01 ng/ml). The mean LH responses in non-working rams tends to increase at a later time than increases in high performing rams, but always remains below the high performers in value (see FIG. 3).

Repeatable effects. There is an effect of season on the hormone response by the rams. Hormone responses to naloxone treatment are similar between high performing and non-working rams in June (P>0.4). There is a ram class/by season of year interaction (P<0.01) for samples evaluated for testosterone response to naloxone at 30, 45, and 60-min post-naloxone treatment. This interaction results from higher testosterone values in high-performing versus non-working rams in November (P<0.01). These differences are not as apparent in June. The same rams were tested over two breeding seasons. There was an effect of year on the responses (P<0.05) but no ram class by year interaction. In Table 1, the accuracy of predicting high sexual and non-working rams using both LH and testosterone is shown. The numbers in each cell represent the data from individuals combined over two consecutive years.

The best predictor of sexual performance is using both LH and testosterone concentrations. Using LH concentration values at 15 minutes post naloxone treatment times the concentration of testosterone at 60 minutes provides the best predictor of both sexual performance and non-working rams. Values of 5.4 and above are sexual performing rams and value below 5.4 is non-working rams.

TABLE 1

Accuracy of predicting sexually working (actual worker) and non-working rams using luteinizing hormone (LH) and testosterone (T) response to naloxone injection [a,b]

| Group | Actual Non-workers | Actual Workers | Totals | Results |
|---|---|---|---|---|
| Group predicted to be Workers | 32 | 12 | 44 | Group consists of 73% correctly identified Non-workers and 27% incorrectly identified Workers |
| Group predicted to be Workers | 10 | 42 | 52 | Group consists of 81% correctly identified Workers and 19% incorrectly identified Non-workers |
| Totals | 42 | 54 | 96 | Accuracy of prediction = (32 + 42)/ 96*100 = 77.1% |

[a]All rams were libido tested with 3 estrus ewes per 30-min test a total of 18 times.
Workers achieved >0.2 ejaculations per test (range = 0.3 to 3.8; avg = 2.7). Non-workers never mounted or ejaculated in any of the 18 tests.
LH measured by RIA in blood plasma samples collected 15 min after naloxone injection.
T measured by RIA in blood plasma samples collected at 60 min after naloxone injection.
LH x T = index. Rams with an index less than or equal to 5.4 were considered to be non-workers.
[b]$X^2 = 27.72$; $p \leq 0.005$
Index = [LH$_{time\ at\ 15\ minutes}$] X [T$_{time\ at\ 60\ minutes}$], Index >5.4 = none working ram.

Literature Cited

D'Occhio, J. M and D. E. Brooks. 1976. The influence of androgens and estrogens on mating behavior in male sheep *Theriogenology* 6:6.

Ebling, F J P, Lincoln G. A, Martin G B, and Taylor P L. 1987. LHRH and B-endorphin in the hypothalamus of the ram in relation to photoperiod and reproductive activity. *Domestic Animal Endocrinology* 4: 149–156.

Fitzgerald J. A and Perkins, A. 1994. Effect of Morphine and naloxone on LH response and sexual behavior of rams (ovis aries). *Domestic Animal Endocrinology* 11(3) :271–279.

Gessa, G. L., Paglietti E, and Quarantotti B P. 1979. Induction of copulatory behavior in sexually inactive rats by naloxone. *Science* 204:203–205.

Hulet, C V., Blackwell R L, and Ercanbrack S K. 1964. Observations on sexually inhibited rams. *J. Animal Science* 23:1095.

Kilgour R J and Whale R G. 1980. The relation between mating activity of rams in pens and subsequent flock mating performance. *Australian Journal of Experimental Agriculture and Animal Husbandry* 20:5.

Knight, T W. 1973. The effect of the androgen status of rams on sexual activity and fructose concentration in the semen. *Australian Journal of Agriculture Resources* 24:573.

Meites J. Bruni J F, Van Uugt D A, and Smith A F. 1979. Relation of endogenous opioid peptides and morphine to neuroendocrine function. *Life Science* 24:1325.

Perkins, A., Fitzgerald J A, and Price, E O. 1992. Luteinizing hormone and testosterone response of sexually active and inactive rams. *Journal of Animal Science* 70:2086–2093.

Perkins, A., Fitzgerald, J A, and Price, E O. 1992. Sexual performance of rams in serving capacity tests predicts success in pasture mating. *Journal of Animal Science* 70:2722.

The literature cited above are incorporated by reference in their entirety.

We claim:

1. A method of discriminating sexually active male mammals from non-working male mammals, the method comprising:
   (a) administering naloxone to individual male mammals in an amount sufficient to elicit a measurable increase in levels of luteinizing hormone and testosterone,
   (b) waiting for a period of time sufficient to elicit a measurable increase in levels of luteinizing hormone and testosterone,
   (c) taking an aliquot of blood to test levels of luteinizing hormone and testosterone,
   (d) measuring the levels of luteinizing hormone and testosterone, and
   (e) classifying individual male mammals as sexually active or non-working based on the levels of luteinizing hormone and testosterone.

2. The method of claim 1 further comprising selecting sexually active individual male mammals based on the levels of luteinizing hormone and testosterone measured in response to naloxone administration.

3. The method of claim 1, wherein the method of administration of naloxone is oral, aerosol, by catheter; or by intramuscular, intraperitoneal, or intravenous injection.

4. The method of claim 1, wherein the amount of naloxone administered ranges from 0.10–2.5 $\mu$mg/kg body weight.

5. The method of claim 4, wherein the amount of naloxone administered ranges from 0.25–1.5 mg/kg body weight.

6. The method of claim 1, wherein the period of time sufficient to elicit a measurable increase in levels of luteinizing hormone is at least 15 minutes.

7. The method of claim 1, wherein the period of time sufficient to elicit a measurable increase in levels of testosterone is at least 30 minutes.

8. The method of claim 1, wherein the aliquot of blood is sufficient to give a reproducibly accurate measure of the levels of luteinizing hormone and testosterone.

9. The method of claim 1, wherein the levels of luteinizing hormone and testosterone are measured by radioimmunoassay or by enzyme-linked immunosorbent assay.

10. The method of claim 1, wherein the individual male mammal is classified as sexually active or non-working based on whether the individual's index score falls within a higher or lower class of a bimodal distribution for a group of naloxone-challenged individuals whose luteinizing hormone and testosterone response is described by the formula:

$$\text{Index} = [LH_{time \geq 15\ minutes}] \times [T_{time \geq 45\ minutes}].$$

11. The method of claim 10, wherein a sexually active male mammal is an individual whose index score falls within the higher class of a bimodal distribution of a group of naloxone-challenged individuals whose luteinizing hormone and testosterone response is described by the formula:

$$\text{Index} = [LH_{time \geq 15\ minutes}] \times [T_{time \geq 45\ minutes}].$$

12. The method of claim 10, wherein a non-working male mammal is an individual whose index score falls within the lower class of a bimodal distribution of a group of naloxone-challenged individuals whose luteinizing hormone and testosterone response is described by the formula:

$$\text{Index} = [LH_{time \geq 15\ minutes}] \times [T_{time \geq 45\ minutes}].$$

13. The method of claim 1, wherein the male mammals are sheep.

14. A test kit for determining the levels of luteinizing hormone and testosterone in individuals following administration of naloxone according to the method steps (a) through (d) of claim 1, the kit comprising:
   (a) naloxone in a composition prepared for delivery to test the individual; and
   (b) directions instructing the administration of naloxone according to the method steps (a) through (d) of claim 1 and interpretation of the results to classify the test individual as sexually active or non-working.

15. A test kit for determining the levels of luteinizing hormone and testosterone in individuals following administration of naloxone according to the method steps (a) through (e) of claim 1, the kit comprising:
   (a) naloxone in a composition prepared for delivery to test the individual;
   (b) reagents used to measure levels of luteinizing hormone and testosterone; and
   (c) directions instructing the administration of naloxone and method of measuring the levels of luteinizing hormone and testosterone according to the method steps (a) through (e) of claim 1, and interpretation of the results to classify the test individual as sexually active or non-working.

* * * * *